(12) United States Patent
Connolly et al.

(10) Patent No.: US 11,191,464 B2
(45) Date of Patent: Dec. 7, 2021

(54) DEVICE SYSTEM AND METHOD FOR FLUID SAMPLE COLLECTION

(71) Applicant: Integrated Nano-Technologies, Inc., Henrietta, NY (US)

(72) Inventors: Dennis M. Connolly, Rochester, NY (US); Richard S. Murante, Rochester, NY (US); Nathaniel E. Wescott, West Henrietta, NY (US)

(73) Assignee: Integrated Nano-Technologies, Inc., Henrietta, NY (US)

( * ) Notice: Subject to any disclaimer, the term of this patent is extended or adjusted under 35 U.S.C. 154(b) by 467 days.

(21) Appl. No.: 16/093,317

(22) PCT Filed: Apr. 14, 2017

(86) PCT No.: PCT/US2017/027651
§ 371 (c)(1),
(2) Date: Oct. 12, 2018

(87) PCT Pub. No.: WO2017/181022
PCT Pub. Date: Oct. 19, 2017

(65) Prior Publication Data
US 2019/0200908 A1 Jul. 4, 2019

Related U.S. Application Data

(60) Provisional application No. 62/322,840, filed on Apr. 15, 2016.

(51) Int. Cl.
*A61B 5/15* (2006.01)
*A61B 5/151* (2006.01)
(Continued)

(52) U.S. Cl.
CPC .... *A61B 5/150022* (2013.01); *A61B 5/15113* (2013.01); *A61B 5/15144* (2013.01);
(Continued)

(58) Field of Classification Search
CPC ........ A61B 5/150022; A61B 5/150396; A61B 5/150503; A61B 5/150732; A61B 5/15113; A61B 5/15144; G01N 1/14
See application file for complete search history.

(56) References Cited

U.S. PATENT DOCUMENTS 4,609,371 A   9/1986 Pizzino
5,965,453 A  10/1999 Skiffington et al.
(Continued)

FOREIGN PATENT DOCUMENTS

EP   0693560 A2   1/1996
EP   0693560 A2   1/2006

OTHER PUBLICATIONS

International Search Report/Written Opinion; Application No. PCT/US2017/027651; filed Apr. 14, 2017; dated Jul. 12, 2017; Integrated Nano-Technologies, Inc.; (16 pages).
(Continued)

*Primary Examiner* — Daniel L Cerioni
(74) *Attorney, Agent, or Firm* — Barclay Damon LLP

(57) ABSTRACT

A system and method for preparing a diagnostic fluid sample for use with a fluid assay system. The method comprises the steps of: amplifying the fluid sample to increase the number of cells subject to being tested; drawing a first volume of the fluid sample into a first syringe of a dual-barrel syringe and dispensing the first volume of the fluid sample through a media filter. The method further comprises the steps of placing the bacteria-laced filter into a lysis module; dispensing a first portion of a lysis buffer into the lysis module from the second syringe of the dual-barrel syringe; and dispensing a second portion of the lysis buffer through the media filter into a disposable cartridge of a fluid assay system.

5 Claims, 13 Drawing Sheets

(51) Int. Cl.
*G01N 1/14* (2006.01)
*G01N 1/10* (2006.01)

(52) U.S. Cl.
CPC .. *A61B 5/150305* (2013.01); *A61B 5/150396* (2013.01); *A61B 5/150503* (2013.01); *A61B 5/150732* (2013.01); *G01N 1/14* (2013.01); *G01N 2001/1056* (2013.01)

(56) References Cited

U.S. PATENT DOCUMENTS

| | | | |
|---|---|---|---|
| 6,187,530 B1* | 2/2001 | Scholin | G01N 1/14 422/50 |
| 2003/0109057 A1 | 6/2003 | Dicesare et al. | |
| 2004/0152206 A1 | 8/2004 | Davis et al. | |
| 2014/0099646 A1* | 4/2014 | Connolly | B01L 3/502 435/6.12 |
| 2017/0002399 A1* | 1/2017 | Eberhart | B01L 3/502707 |

OTHER PUBLICATIONS

International Preliminary Report on Patentability; Application No. PCT/US2017/027651; filed Apr. 14, 2017; dated Oct. 16, 2018; Integrated Nano-Technologies, Inc. (14 pages).

PCT/US2017/027651; filed Apr. 14, 2017; International Search Report dated Jul. 12, 2017; Integrated Nano-Technologies, Inc.; (3 pages).

* cited by examiner

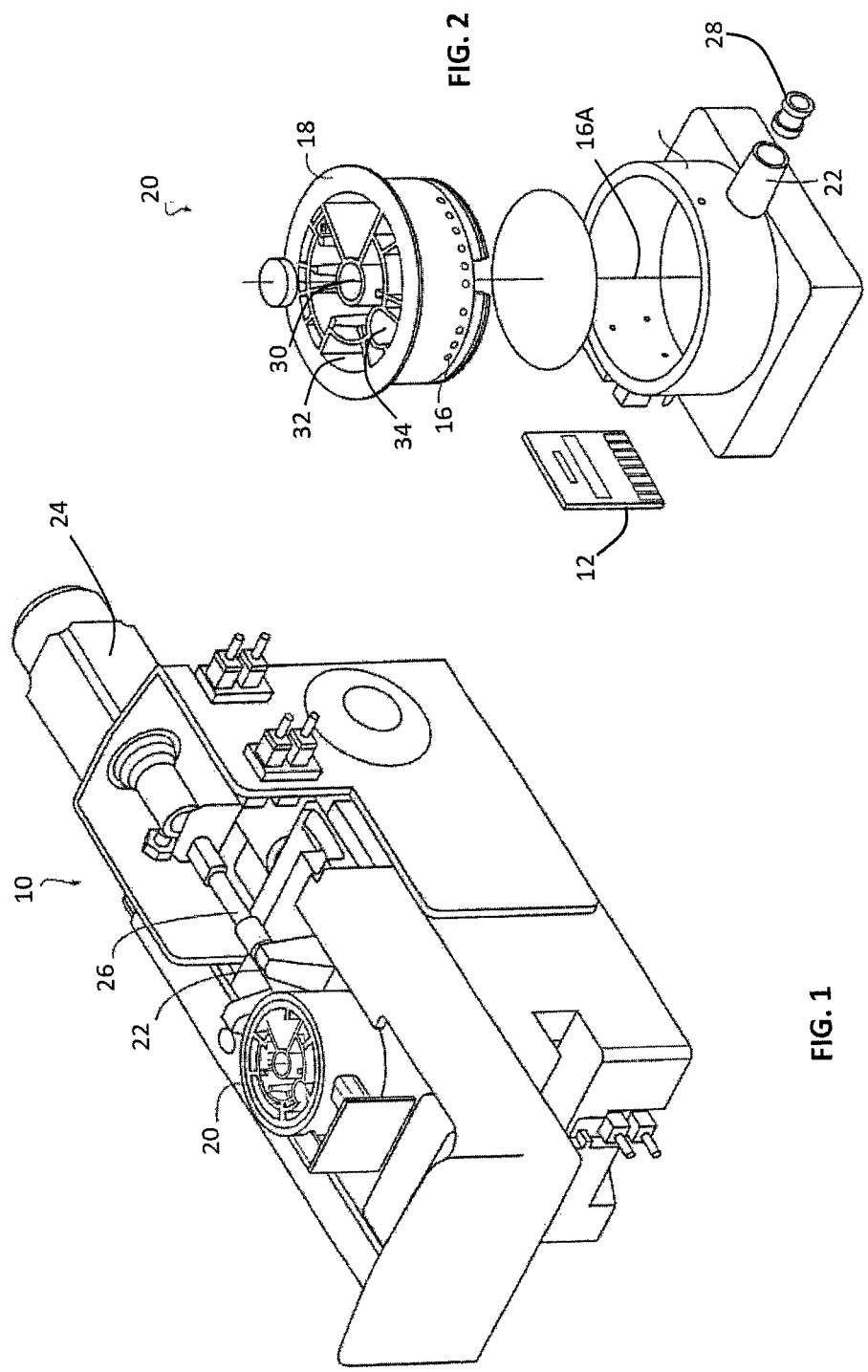

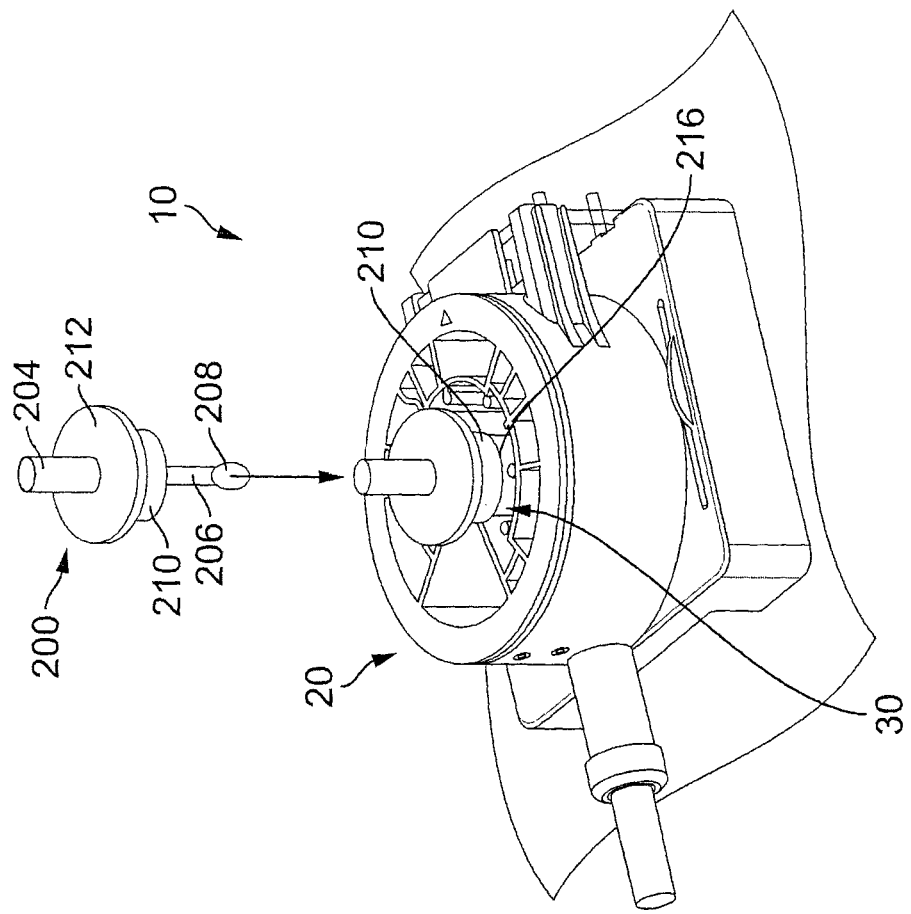
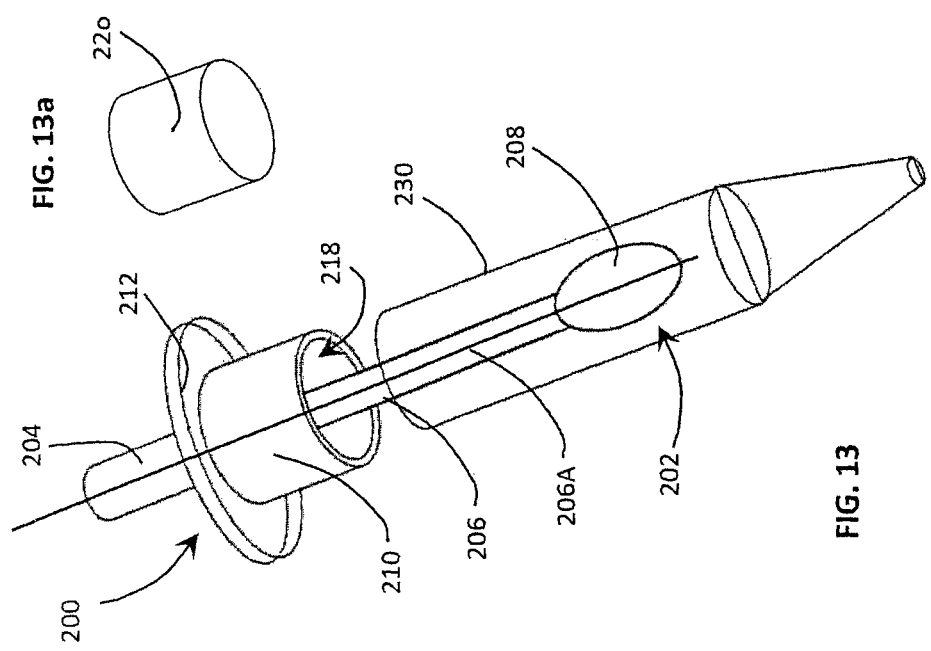
FIG. 13a
FIG. 13
FIG. 14

DEVICE SYSTEM AND METHOD FOR FLUID SAMPLE COLLECTION

CROSS-REFERENCE TO RELATED APPLICATIONS

This application is a Non-Provisional Utility Patent application which claims priority from a first U.S. Provisional Patent Application Ser. No. 62/322,840, filed Apr. 15, 2016 entitled "Blood Sample Device" and U.S. Provisional Patent Application Ser. No. 62/322,843, filed Apr. 15, 2016 entitled "Food Sample Device." The contents of the aforementioned applications are hereby incorporated by reference in their entirety.

This application relates to U.S. patent application Ser. No. 15/157,584 filed May 18, 2016 entitled "Method and System for Sample Preparation" which is a continuation of U.S. Non-Provisional patent application Ser. No. 14/056,603, filed Oct. 17, 2013, now U.S. Pat. No. 9,347,086, which claims priority to U.S. Provisional Patent Application Ser. No. 61/715,003, filed Oct. 17, 2012, which is a continuation-in-part of U.S. patent application Ser. No. 12/785,864, filed May 23, 2010, now U.S. Pat. No. 8,663,918, which claims priority to U.S. Provisional Patent Application Ser. No. 61/180,494, filed May 22, 2009, and which is also a continuation-in-part of U.S. patent application Ser. No. 12/754,205, filed Apr. 5, 2010, now U.S. Pat. No. 8,716,006, which claims priority to U.S. Provisional Patent Application Ser. No. 61/166,519, filed Apr. 3, 2009. The contents of the aforementioned applications are hereby incorporated by reference in their entirety.

TECHNICAL FIELD

This invention relates to a device, system, and method for analyzing biological samples. In one embodiment, a device, system and method for collecting samples is disclosed for use in combination with multi-chambered disposable cartridges for use in assaying blood samples. In another embodiment, a system and method is disclosed for use in combination with multi-chambered disposable cartridges for use in assaying food samples.

BACKGROUND

There is continuing interest to improve testing methodologies, facilitate collection and decrease the time associated with clinical laboratories. Particular testing requires that a sample be disrupted to extract nucleic acid molecules such as DNA or RNA.

The number of diagnostic tests performed annually has increased exponentially in the past decade. The use of molecular diagnostics and gene sequencing in research and medical diagnostics is also rapidly growing. For example, DNA testing has also exploded in view of the growing interest in establishing and tracking the medical history and/or ancestry of a family. Many, if not all of these assays, could benefit from a rapid sample preparation process that is easy to use, requires no operator intervention, is cost effective and is sensitive to a small sample size.

Sample collection and preparation is a major cost component of conducting real-time Polymerase Chain Reaction (PCR), gene sequencing and hybridization testing. In addition to cost, delays can lead to the spread of infectious diseases, where time is a critical component to its containment/abatement. In addition to delaying the test results, such activities divert much-needed skilled resources from the laboratory to the lower-skilled activities associated with proper collection, storage and delivery.

For example, a portable molecular diagnostic system could be operated by minimally trained personnel (such as described in US 2014/0099646 A1) and have value with regard to disease surveillance. However, the adoption of such portable systems can be limited/constrained by current methods of sample collection, which require trained personnel to permit safe and effective handling of blood samples for analysis.

A need, therefore, exists for an improved device, system and method for collection, preparation and testing of fluid samples, facilitates the use of minimally-trained personnel, facilitates the testing of both blood and food samples, and may be used in combination with a portable molecular diagnostic system.

SUMMARY

The present disclosure relates to a sample collection/carrier device and method for using the same when assaying fluid samples, such as blood and food samples.

In one embodiment, a blood collection assembly is provided to facilitate the assay of a blood sample, comprising: (i) an absorptive media configured to collect and release the blood sample, (ii) a cartridge defining a cavity and a blood-sampling end configured to hold the absorptive media against a dermal membrane containing the blood sample, (iii) a lancet disposed within the cavity and having a lance at one end thereof, and (iv) a plunger configured to extend and retract the lancet through the absorptive media to lance the dermal membrane and collect the blood sample within the absorptive media. The cartridge containing the blood-filled, absorptive media is configured to be placed into a blood assay device for extraction or elution of the blood sample from the absorptive filter.

In another embodiment, a device is provided to facilitate the assay of a fluid sample, comprising: (i) an absorptive media configured to collect and release the fluid sample, and (ii) a carrier configured to: (a) hold the absorptive media in contact with the fluid sample during collection, (b) carry the absorptive media into an apparatus for assaying the fluid sample, and (c) produce a fluid-retaining barrier with the apparatus while assaying the fluid sample.

In another embodiment, a dual-barrel syringe is provided to facilitate the preparation of a diagnostic fluid sample, comprising: (i) a first syringe operative to draw a quantity of the fluid sample, (ii) a second syringe containing a lysis buffer, the first and second syringes defining first and second barrels, respectively, which are juxtaposed and share a common wall, and (iii) a valve mechanism containing a nozzle which may be rotated into in fluid communication with an opening in each of the first and second barrels.

In yet another embodiment, a food assay system is provided to facilitate the assay of a fluid sample, comprising: an absorptive media configured to collect and release the fluid sample, and a disposable assay cartridge configured to assay the fluid sample for detecting the presence of a select attribute. The disposable cartridge has least one sample chamber disposed in fluid communication with at least one assay chamber containing at least one assay chemical facilitating the detection of the select attribute. The food assay system comprises, a fluid collection carrier configured to: (i) hold the absorptive media in contact with the fluid sample during collection, (ii) carry the absorptive media into the disposable assay cartridge for assaying the fluid sample, and (iii) produce a fluid-retaining barrier with the disposable assay cartridge while assaying the fluid sample. The fluid collection carrier is configured to be placed into the at least one sample chamber such that the at least one assay chemical is disposed in combination with the fluid sample to determine whether the select attribute is present.

In yet another embodiment, a method for collecting a blood sample is provided comprising the steps of: providing a cartridge having a filter-retaining end and a plunger/lancet assembly, loading the filter-retaining end with an absorptive media capable of absorbing a fixed-quantity of blood and placing the absorptive media of the assembly into contact with the skin of a patient. The method further comprises the steps of: activating the plunger/lancet assembly to cause a lancet thereof to penetrate the skin to effect collection of the fixed-quantity of blood into the absorptive media, and placing the assembly and the blood-filled, absorptive media into a blood assaying device.

In yet another embodiment, a method is provided for preparing a diagnostic fluid sample for use with a fluid assay system. The method comprises the steps of: amplifying the fluid sample to increase the number of cells subject to being tested, drawing a first volume of the fluid sample into a first syringe of a dual-barrel syringe and dispensing the first volume of the fluid sample through a media filter. The method further comprises the steps of: placing the bacteria-laced filter into a lysis module, dispensing a first portion of a lysis buffer into the lysis module from the second syringe of the dual-barrel syringe, and dispensing a second portion of the lysis buffer through the media filter into a disposable cartridge of a fluid assay system.

BRIEF DESCRIPTION OF THE DRAWINGS

The present invention is disclosed with reference to the accompanying drawings, wherein:

FIG. 1 is a perspective view of a portable diagnostic assay system operative to accept one of a plurality of disposable cartridges configured to test fluid samples of collected blood or food samples.

FIG. 2 is an exploded perspective view of one of the disposable cartridges configured to test the biological samples.

FIG. 13 depicts a novel fluid collection device including an absorptive media disposed at the tip end of a carrier configured to: (i) hold the absorptive media in contact with the fluid sample during collection, (ii) carry the absorptive media into a portable fluid assaying system, and (iii) produce a fluid-tight or fluid-retaining seal/barrier with the portable fluid assaying system while performing an analysis of the fluid sample.

FIG. 13a depicts an alternate embodiment of the carrier including a plug functionally replacing a cap to produce the fluid-tight or fluid-retaining seal barrier with the portable fluid assaying system.

FIG. 14 depicts the fluid collection device being placed into, and seated within, a disposable cartridge of a portable diagnostic assay system.

Corresponding reference characters indicate corresponding parts throughout the several views. The examples set out herein illustrate several embodiments of the invention but should not be construed as limiting the scope of the invention in any manner.

DETAILED DESCRIPTION

Figure 4:
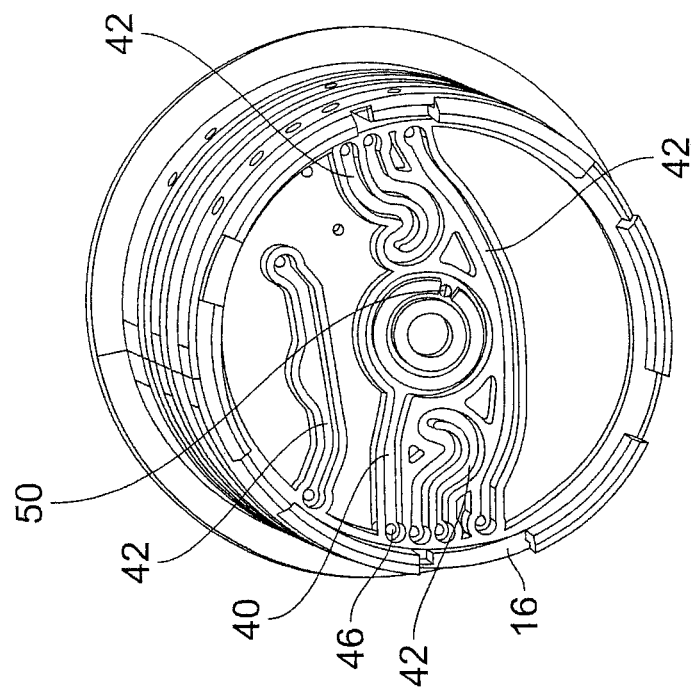
FIG. 4 is a bottom view of the disposable cartridge shown in FIG. 3 illustrating a variety of channels operative to move at least a portion of the fluid sample from one chamber to another the purpose of performing multiple operations on the fluid sample.

A blood collection assembly is described for use in combination with a portable/automated assay system such as that described in commonly-owned, co-pending U.S. patent application Ser. No. 15/157,584 filed May 18, 2016 entitled "Method and System for Sample Preparation" which is hereby included by reference in its entirety. The blood collection assembly may be used in combination with a variety of blood diagnostic cartridges which may be used to detect any of a variety of diseases which may be found in a blood specimen. For example, such blood diagnostic cartridges may be dedicated cartridges useful for detecting Hepatitis, Autoimmune Deficiency Syndrome (AIDS/HIV), Diabetes, Leukemia, Graves, Lupus, Multiple Myeloma, etc., just naming a small fraction of the various blood borne diseases that the portable/automated assay system may be configured to detect.

More specifically, and referring to FIGS. 1 and 2, the system employs the use of a portable assay system 10 which receives any one of a variety of disposable assay cartridges 20, each selectively configured for detecting a particular attribute of a fluid sample. The portable assay system 10 includes one or more linear and rotary actuators operative to move fluids into, and out of, various compartments or chambers of the disposable assay cartridge 20 for the purpose of identifying or detecting a fluid attribute. More specifically, a signal processor 14, i.e., a PC board, controls a rotary actuator (not shown) of the portable assay system 10 so as to align one of a variety of ports 16, disposed about a cylindrical rotor 18, with a syringe barrel 22 of the assay cartridge 20. Furthermore, the processor 14 controls a Linear Variable Displacement Transducer (LVDT) 24, to displace a shaft 26 for the purpose of developing pressure i.e., positive or negative (vacuum) in the syringe barrel 22. That is, the shaft 26 displaces a plunger 28 within the syringe 22 to move and or admix fluids contained in one or more of the chambers 30, 32.

The disposable cartridge 20 provides an automated process for preparing the fluid sample for analysis and/or performing the fluid sample analysis. The sample preparation process allows for disruption of cells, sizing of DNA and RNA, and concentration/clean-up of the material for analysis. More specifically, the sample preparation process of the instant disclosure prepares fragments of DNA and RNA in a size range of between about 100 and 10,000 base pairs. The chambers can be used to deliver the reagents necessary for end-repair and kinase treatment. Enzymes may be stored dry and rehydrated in the disposable cartridge, or added to the disposable cartridge, just prior to use. The use of a rotary design allows for a single plunger to draw and dispense fluid samples without the need for a complex system of valves to open and close at various times. This greatly reduces potential for leaks and failure of the device compared to conventional systems. It will also be appreciated that the system greatly diminishes the potential for human error.

Figure 3:
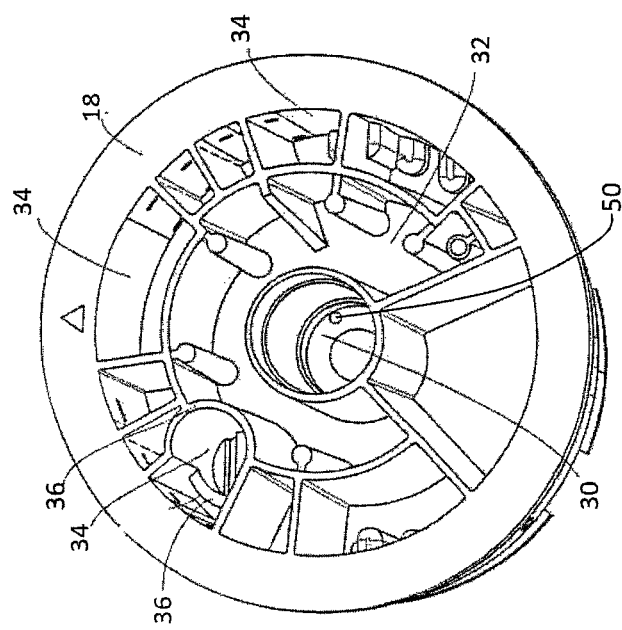
FIG. 3 is a top view of the one of the disposable cartridges illustrating a variety of assay chambers including a central assay chamber, one of which contains an assay chemical suitable to breakdown the fluid sample to detect a particular blood attribute.
Figure 6:
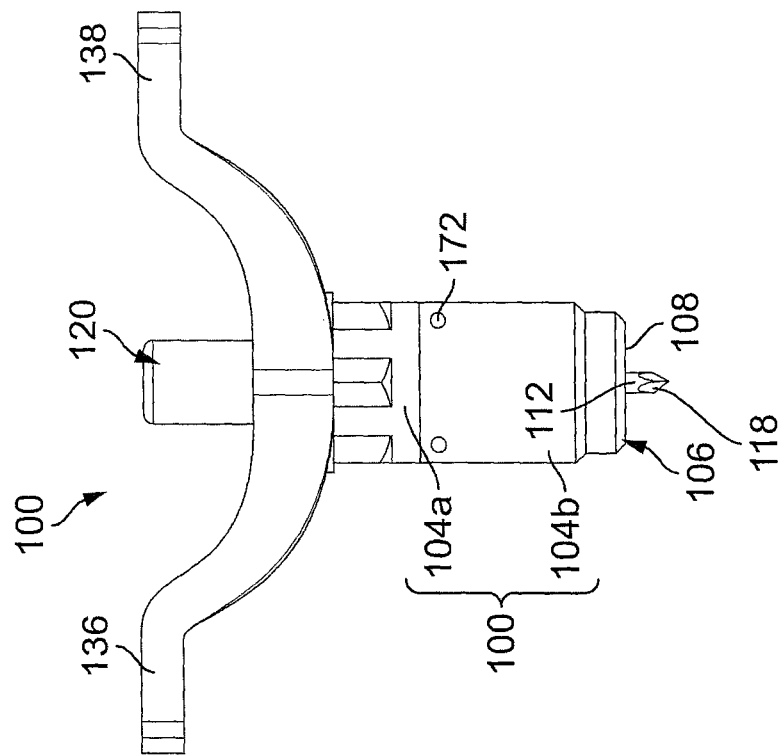
FIGS. 5 and 6 are perspective and profile views, respectively, of a novel blood collection assembly according to one embodiment of the disclosure including: a body, a blood-collection end configured to secure an absorptive media, and a trigger operative to activate the extension and retraction of a lancet disposed within a cavity of the body and projecting through an aperture in the absorptive media to effect the collection of a blood sample.
Figure 5:
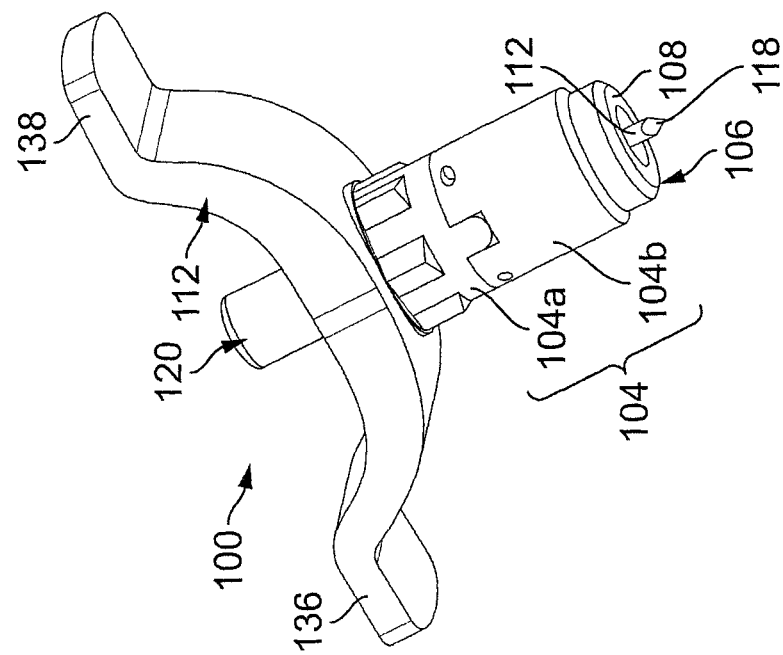
Figure 7:
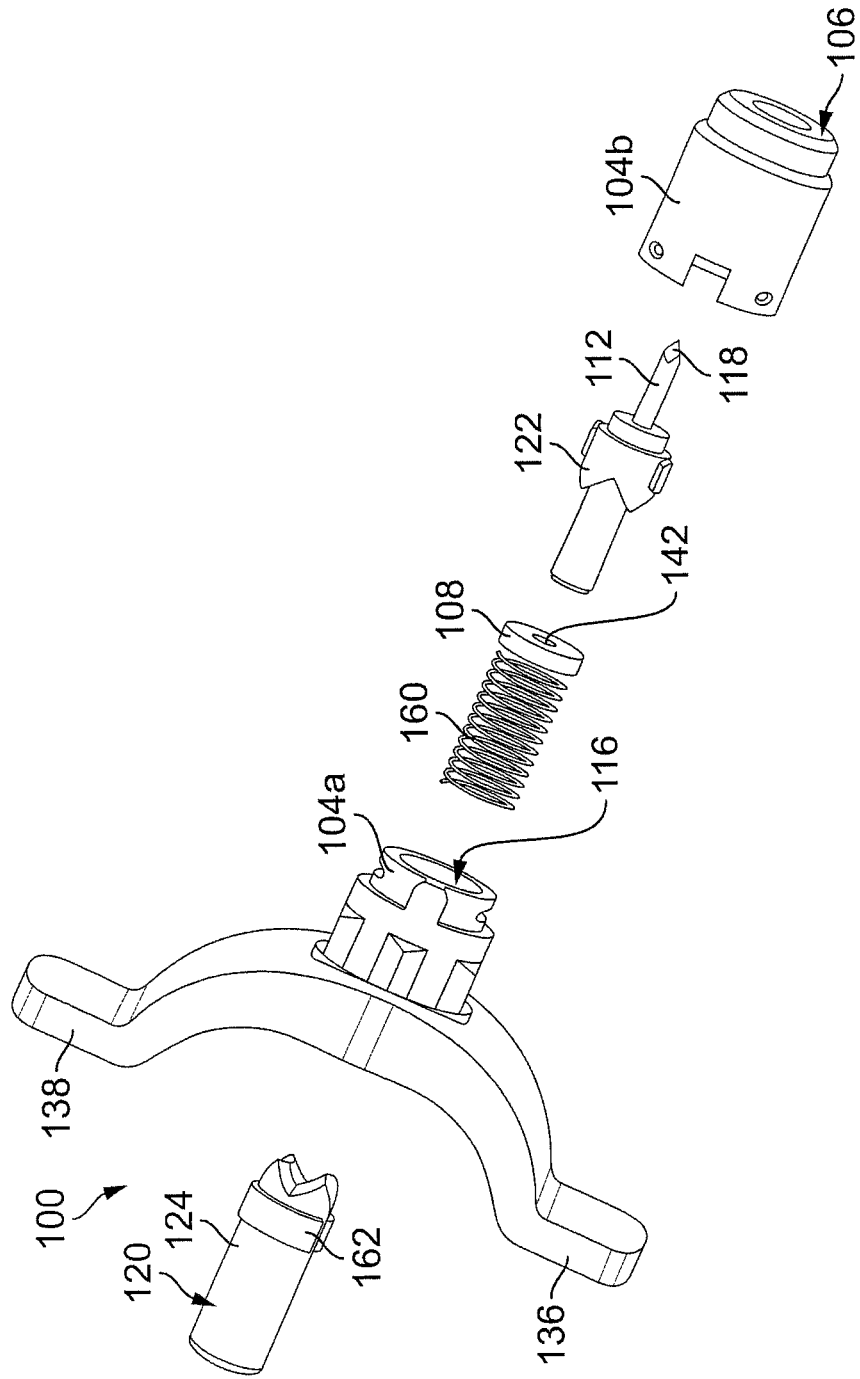
FIG. 7 is an exploded view of the blood collection assembly including an upper body including a pair of laterally projecting finger flanges, a lower body including a blood-retention end, a trigger portion, a piston portion, an absorptive media and a coil spring.
Figure 9:
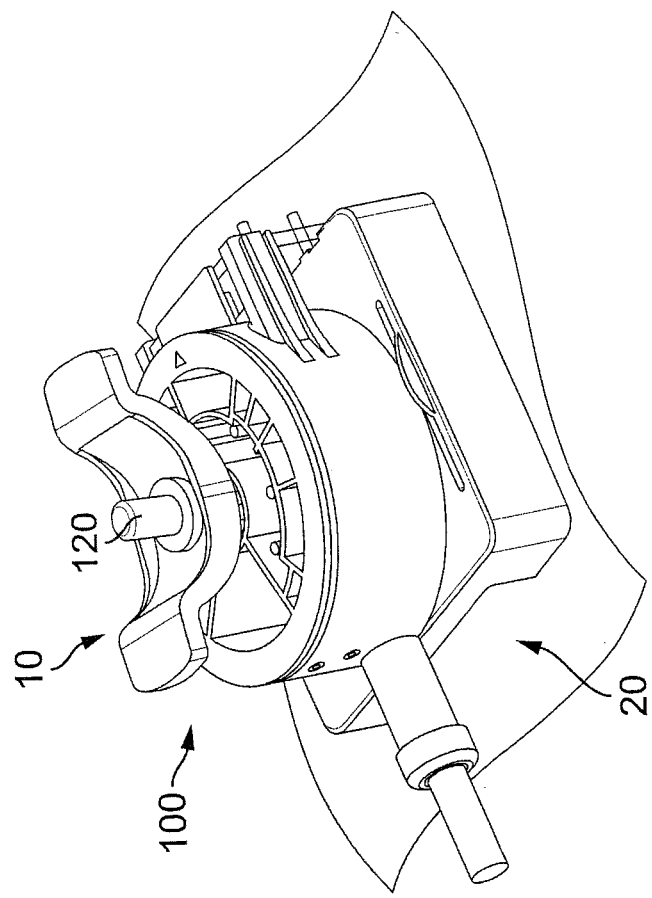
FIG. 9 depicts the blood collection assembly seated in the disposable cartridge of the portable diagnostic assay system.
Figure 8:
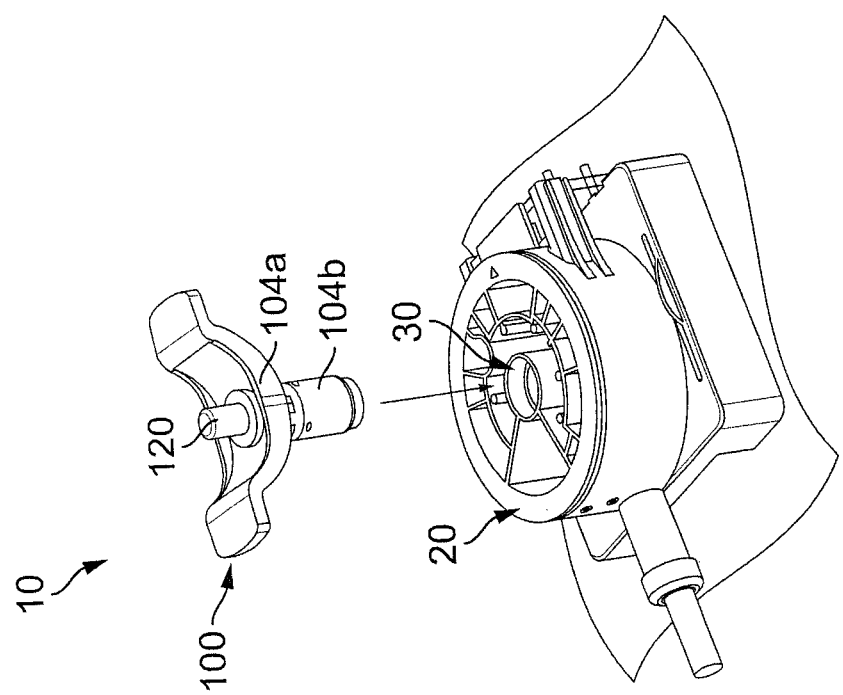
FIG. 8 depicts the blood collection assembly being placed into a disposable cartridge of a portable diagnostic assay system.

In FIGS. 3 and 4, the cylindrical rotor 18 includes a central chamber 30 and a plurality of assay chambers 32, 34 surrounded, and separated by, one or more radial or circumferential walls 36. In the described embodiment, the central chamber 30 receives the fluid sample while the surrounding chambers 32, 34 may contain a premeasured assay chemical or reagent for the purpose of detecting an attribute of the fluid sample. The chemical or reagents may be initially dry and rehydrated immediately prior to conducting a test. Some of the chambers 32, 34 may be open to allow the introduction of an assay chemical while an assay procedure is underway or in process. The chambers 30, 32, 34 are disposed in fluid communication, e.g., from one of the ports 16 to one of the chambers 30, 32, 34, by channels 40, 42 molded in an underside surface 42 of the rotor 18. For example, a port 16, corresponding to aperture 42, may be in fluid communication with the central chamber 30, via aperture 50.

Blood Collection Assembly

In FIGS. 5-8, an embodiment of a novel blood collection assembly 100 comprises: (i) a body 104 having a blood-sampling end 106 configured to hold an absorptive media or filter 108, (ii) a lancet 112 disposed within a cavity 116 (See FIG. 7) of the body 104 and having a lance 118 at one end thereof, and (iii) a plunger or plunger assembly 120 configured to extend and retract the lancet 112 through the absorptive media or filter 108 to lance a dermal membrane, (i.e., the skin of a patient), and collect a blood sample within the absorptive media or filter 108. Once a blood sample has been collected, the body 104 containing the blood-filled, absorptive media or filter 108 is configured to be placed into a blood assay device 10, i.e., the fluid sample chamber 30 of the disposable cartridge 20. This step may be performed immediately, or involve the sterile packaging/storing and/or transport of the blood sample, for subsequent analysis. Notwithstanding the time between collection and analysis, the blood collection assembly 100 is configured to be placed into a blood assay device 10 to elute the blood from the absorptive media 108. Furthermore, the blood collection assembly closes the sample chamber, i.e., produces a fluid-tight seal or fluid barrier, such that fluids may flow between ports 16 as pressure is developed in the various chambers 30, 32, 34 and channels 40, 42 of the disposable cartridge 20.

In the described embodiment, the body 104 includes an upper body portion 104a and a lower body portion 104b which collectively define the cavity 116. The body 104 is split to allow assembly of the plunger or plunger assembly 120 for insertion into the cavity 116, or to facilitate the replacement/removal of the absorptive media 108. While the absorptive media 108 may be replaced following use, the blood collection assembly of the present disclosure is intended to be disposable, similar to the disposable cartridge that it supplies.

The upper body portion 104a includes a pair of finger-receiving flanges 136, 138 projecting laterally from the body 104 to facilitate handling of the assembly 100 while placing the absorptive media 108 against the dermal membrane or skin. The lower body portion 104b is configured to secure the absorptive media 108 within an annular groove or recess formed at the tip-end of the lower body portion 104b, i.e., at the tip of the blood-sampling end 106 of the body 104.

The lancet 112 comprises a conventional tubular shaft having an end which is cut at a shallow angle, i.e., inclined, to produce a pointed tip end 118. The tip may be machined at an angle to produce a piercing tip, or sharpened to produce a razor-sharp lance 118. One end of the lancet 112 is embedded within a piston portion of the plunger or plunger assembly 120, discussed in greater detail below, while the other end of the lancet 112 faces the absorptive media 108 while disposed within the cavity 116 of the blood collection assembly 100.

The absorptive media 108 may be any material that absorbs and retains a liquid sample (paper, cellulose matrix, etc.) The material can be cut, pleated or woven in any manner to adjust the collected volume. In one embodiment, the absorptive media 108 includes a cellulose fiber filter having cotton linters treated to achieve an alpha cellulose content greater than about ninety-eight percent (98%). Filter materials suitable for use include Whatman Brand filters such as the Whatman FTA Elute series of paper products which facilitates: (i) long-term room temperature DNA preservation, (ii) multiple amplifications from a single sample, and (iii) ease of elution.

In the described embodiment, the absorptive media 108 is an annular ring having an aperture 142 for receiving the lancet 112 upon activation of the plunger 120. While an annular ring is described, the absorptive media may have any shape provided it allows the lancet to penetrate or pass through a portion of the media material.

In one embodiment, the plunger 120 is spring-biased within the cavity 116 of the body 104 to be retracted and extended relative to the body 104. Furthermore, since the lancet 112 is connected to the plunger 120, the lancet 112 may also extend and retract within the cavity 116 to urge the lance 118 through the opening or aperture 142 in the absorptive media 108. In the described embodiment, a coil spring 160 abuts a raised ring-shaped shoulder 162 formed along the outer circumference of the trigger 120, allowing the trigger 120 to be depressed from, and returned to, an extended position. As mentioned in the preceding sentence, inasmuch as the lancet 112 is mounted to the trigger 120, the lancing end 118 may also extend and retract through the opening 142 in the absorptive media 108.

Figure 11:
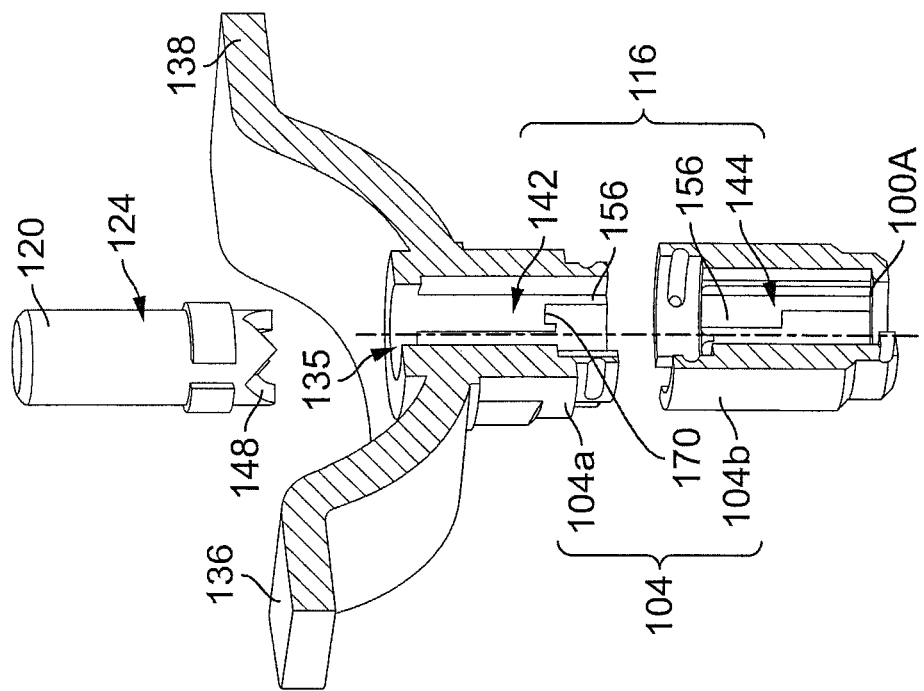
FIG. 11 depicts the cavity of the upper and lower body portions for mounting the plunger and absorptive media of the blood collection assembly.
Figure 10:
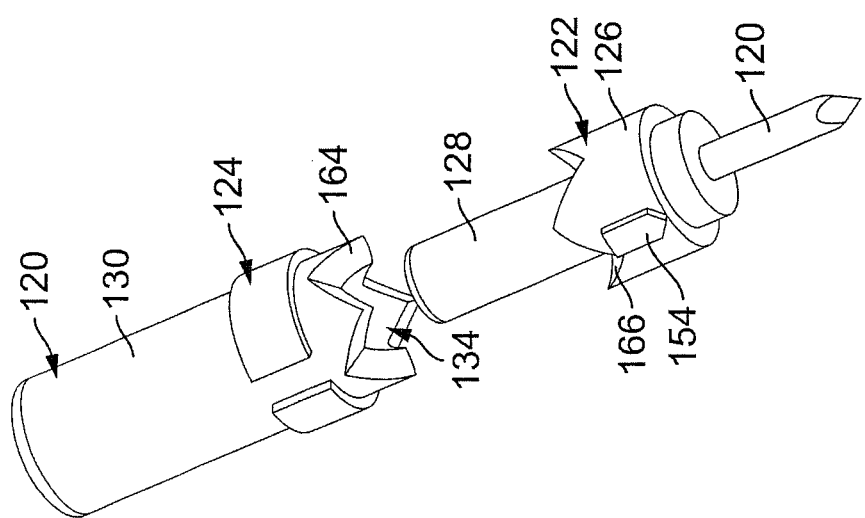
FIG. 10 depicts an isolated perspective view of the trigger and piston portions of the plunger each having a plurality of mating teeth and a telescopic mounting surface for permitting relative motion between the trigger and piston portions.
Figure 12:
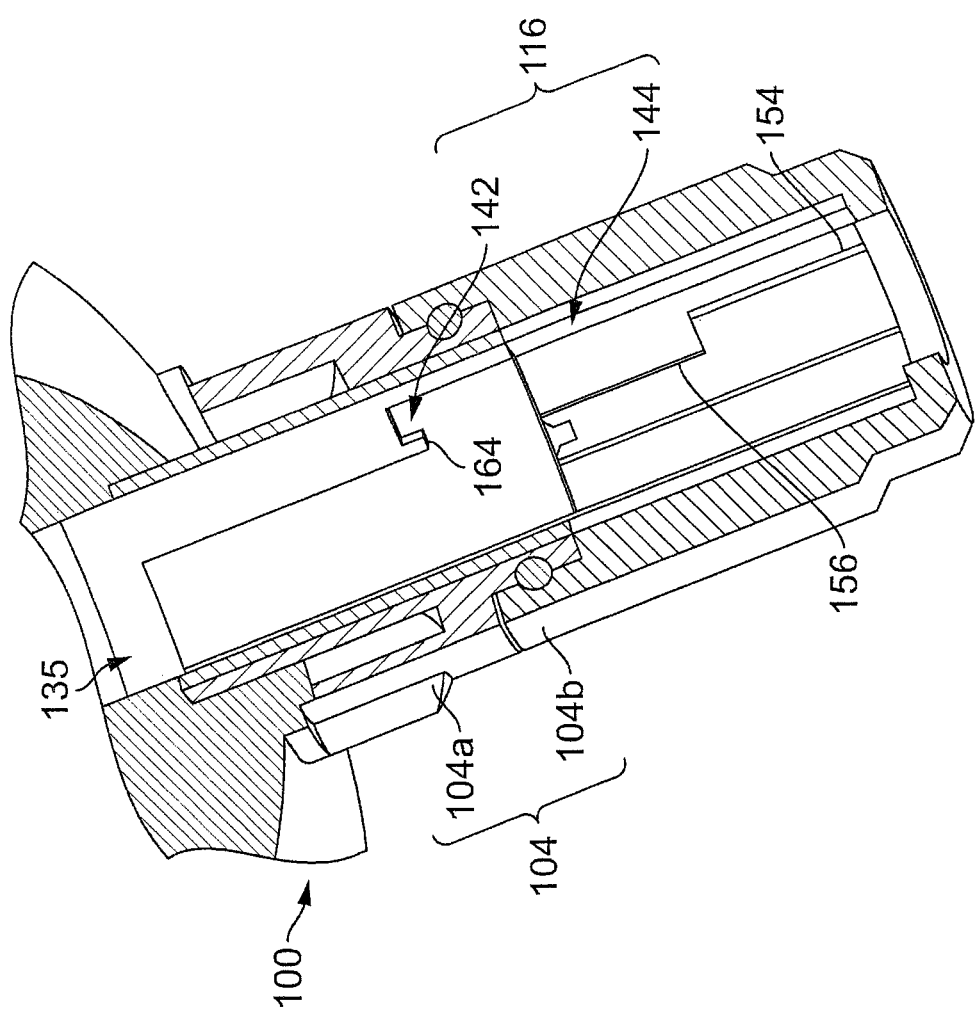
FIG. 12 depicts an enlarged internal view of the cavity depicting guide and retention surfaces for axial translation of the plunger, auto-retraction of the piston portion, and a locking feature of the trigger portion in a depressed or retracted position.

In FIGS. 10-12, the plunger or plunger assembly 120 includes a piston portion 122 and a trigger portion 124. The piston portion 122 (i) defines a first cylindrical surface 126 slidably guided along an internal cylindrical bore or surface 144 of the cavity 116, (ii) defines a second cylindrical surface 128 telescopically mounting within a bore 134 of the trigger portion 124, and (iii) includes a pair of arrow-shaped radial protrusions 154 (FIG. 10) to axially guide the piston portion 122 within axial channels 156, while preventing rotation of the piston portion 122 about an elongate axis 100A (FIG. 11) of the assembly 100. The trigger portion 124 is: (i) disposed between the finger-receiving flanges 136, 138 of the upper body portion 104a of the assembly 100, (ii) slideably guided within a bore 135 in the upper body portion 104a, and (iii) axially guided within the bore 142 (see FIG. 12) by the raised linear guide 156 within the cavity 116.

The piston and trigger portions 122, 124 include first and second crown-shaped teeth 164, 166, respectively, which facilitate the transfer of axial motion between the piston and trigger portions 122, 124 while imparting rotational motion as a consequence of engagement between the inclined surfaces of the crown-shaped teeth 164, 166. Inasmuch as the piston portion 122 employs anti-rotation protrusions 154, the piston portion travels axially within the guide 156 while the trigger portion 124 rotates into a shoulder notch 170. The trigger portion 124 only moves into the notch 170 as the trigger portion 124 moves axially past notch 170 or as the trigger portion 124 moves past a threshold axial location.

The relative rotation between the piston and trigger portions 122, 124 causes the piston portion 122 to recede into the trigger portion 124 as a consequence of the telescopic mount between the piston and trigger portions portion 122, 124. Furthermore, inasmuch as the lancet 112 is seated within the piston portion 124, the lancet 112 "auto-retracts" when the trigger portion 124 rotates under the notch 170. Furthermore, when the trigger portion 124 rotates beneath the notch 170, it is no longer capable of retraction and extension. Accordingly, the trigger piston 124 is "locked" and incapable of a second use. This feature may be desirable to prevent cross-contamination of the blood sample. Alternatively, the lancet 122 may move into a position where it is locked by a housing shoulder to prevent the lancet 112 and the blood collection assembly 100 from being used a second time.

Once a blood sample has been taken, the blood collection assembly 100 is placed within the sample chamber 30 of the disposable cartridge 20. The blood collection assembly 100 may include a sealing ring (not shown) at the tip end of the assembly to facilitate the formation of a fluid-tight seal. Additionally, to augment release and elution of the blood from the absorptive media 108, one or more apertures 172 (see FIG. 6) may be formed in the body 104 to facilitate fluid flow through the absorptive media 108.

Fluid Sample Carrier

In FIGS. 13, 13a, and 14, a novel food assay system and fluid sample carrier 200 includes an absorptive media 208 configured to collect and release or elute a fluid sample when disposed in combination with a disposable cartridge 20 of a food assay system 10. The disposable assay cartridge 20 is essentially the same as was previously described, i.e., the arrangement of chambers, channels, ports, and plungers etc. The principal difference between the disposable assay cartridges 20 relates to the types of biological agents or attributes being assayed. For example, a cartridge 20 may be configured to assay for *salmonella, E. coli*, mad-cows disease, and other food borne pathogens. Additionally, the assembly can be configured to assay West Nile Virus or Lime Disease.

The fluid collection carrier 200 of this embodiment includes a sample collection end 202, a protective handle 204, and a connecting shaft 206 disposed therebetween. The sample collection end 202 includes a media or media filter 220 suitable for absorbing and carrying fluids which are suspected of containing a hazardous or dangerous pathogen.

The absorptive media 208 may be any material that absorbs and retains a liquid sample (paper, cellulose matrix, etc.). In one embodiment, the absorptive media 208 includes a cellulose fiber having cotton linters treated to achieve an alpha cellulose content greater than about ninety-eight percent (98%). Fiber media materials suitable for use include Whatman Brand filters such as the Whatman FTA Elute series of paper products which facilitates long-term room temperature preservation and ease of elution.

In the described embodiment, the absorptive media 208 will have an elliptical shape and be sized to collect a select volume of fluid. While an ellipse is depicted, the absorptive media 208 may have any shape suitable for swabbing a surface or absorbing a standing fluid.

In one embodiment, the carrier 200 comprises a sealing member or cap 210 disposed between the shaft 206 and the protective handle 204. The cap 210 is configured to be disposed over a rim 216 (FIG. 14) of the sample chamber 30 of the disposable cartridge 20 and form a fluid-tight or fluid-retaining seal or barrier between it and the disposable cartridge 20. In the described embodiment, the cap 210 defines a cavity 218 to accept the rim 216 of the disposable cartridge 20. Similar to the previously-described blood collection assembly 100, the carrier 200 forms a seal or barrier with the sample chamber 30 such that the absorptive media 208 may elute the fluid to assay for food-borne diseases, hazardous biological agents, and/or dangerous pathogens.

In another embodiment depicted in FIG. 13a, an elastomer plug 220 functionally replaces the cap 210 to produce the seal or barrier with the sample chamber 30. In this embodiment, the plug 220 is received within the sample chamber 30 and forms a seal with the internal periphery of the sample chamber 30.

In another embodiment, the sealing member 210, 220 forms a fluid-tight seal with a vial 230 configured to maintain the purity or sterility of the fluid sample, both before and after collection. Furthermore, the vial 230 may be filled with a sterile fluid before and/or after sample collection.

The fluid collection carrier 200 is configured to: (i) hold the absorptive media 208 in contact with the fluid sample so as to cause the absorptive media 208 to collect a quantity of the fluid sample; (ii) carry the absorptive media 208 into the disposable assay cartridge 20, and (iii) close an end of the sample chamber 30 to prevent the egress of assay fluids and/or assay chemicals during assay testing.

In the described embodiment, the protective handle 204 includes a flange 212 projecting laterally outboard from an axis 206A defined by the shaft 206. The flange 212 is disposed axially aft, or rearward of, the sealing member 210 and functions to protect a handler from exposure to the food-borne diseases, hazardous biological agents, and/or dangerous pathogens carried within the absorptive media 208.

Dual-Barrel Syringe for Preparation of a Food Sample

Many diagnostic tests, particularly food safety testing, require bacterial growth or amplification of the sample, prior to testing. This is due to the fact that certain agents, particularly those in food, often present very low levels of the biological attribute sought to be tested or detected in a sample. To enhance the probability of detecting the biological attribute, i.e., a test sample with a low Colony Forming Unit (CFU) count, a large sample size, i.e., typically more than ten milliliters (10 ml) can be required. This requirement, however, runs counter to many diagnostic assay systems which are designed for much smaller sample inputs, i.e., typically less than about fifty micro-liters (50 µl.)

To integrate these competing requirements, a multi-barrel syringe 300 in combination with a selector valve 304 may be employed to draw, dispense, expose, and rinse/flush the fluid sample from an initial quantity of a food sample which has been amplified immediately prior to conducting an assay test.

Figure 15:
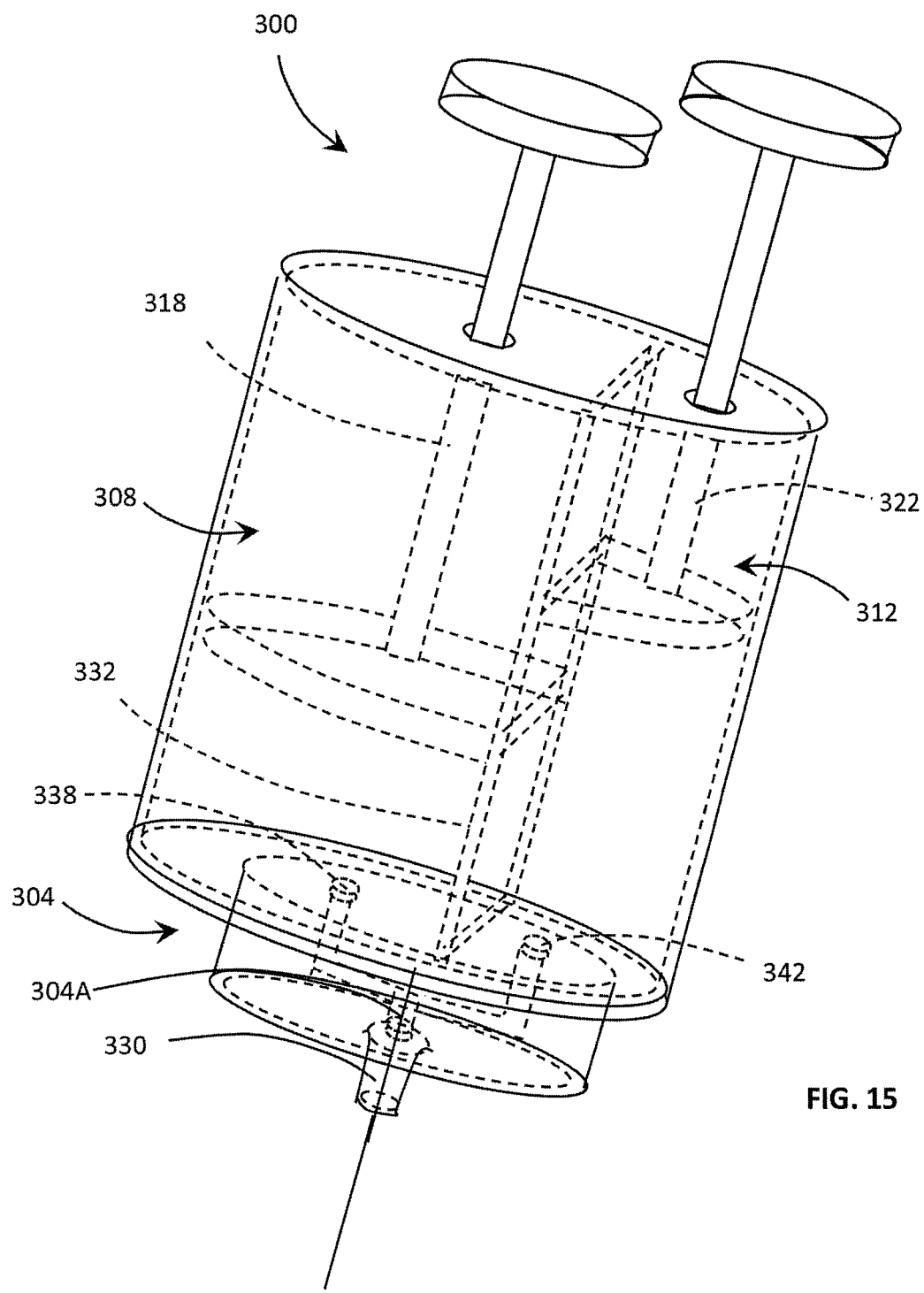
FIG. 15 depicts a perspective view of a dual-barrel syringe facilitating the preparation of a diagnostic fluid sample, including a first syringe operative to draw a quantity of the fluid sample, a second syringe juxtaposed with and sharing a common wall with the first syringe, the second syringe containing a lysis buffer, and a valve mechanism containing a nozzle which may be rotated into fluid communication with an opening in each barrel of the first and second syringe.
Figure 16:
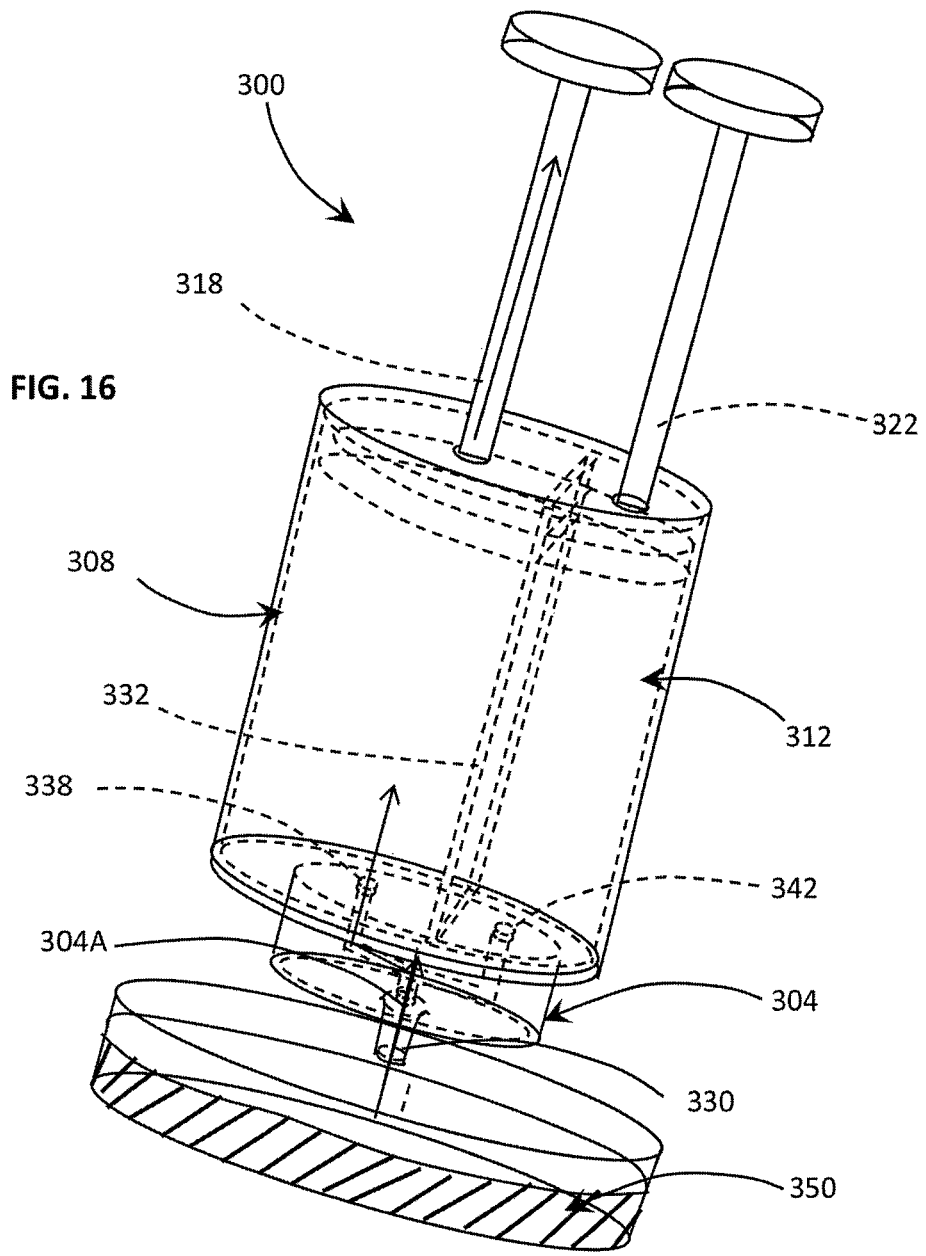
FIGS. 16-19 depict the dual-barrel syringe in various operating positions including drawing, dispensing, exposing and rinsing/flushing the fluid sample in preparation for assay testing within a portable biological assay system.

More specifically, and referring to FIGS. 15 and 16, the syringe 300 comprises first and second barrels 308, 312 having first and second syringe plungers 318, 322, and a selector valve 326 rotatably mounted to an end of the syringe 300 about an axis of rotation 304A and having a syringe nozzle 330. The first and second barrels 308, 312 are juxtaposed, share a common wall 332, and define first and second apertures 338, 342 at an end of each of the first and second barrels 308, 312, respectively.

The first barrel 308 of the dual-barrel syringe 300 is larger than the second barrel 312, and in the described embodiment, the volume of the first barrel 308 is between about five (5) to one-hundred (100) times larger than the volume of the second barrel 312. Furthermore, the first barrel 308 of the dual-barrel syringe 300 is initially empty to allow the first barrel 308 to draw a fluid sample from a biological sample 350 (FIG. 16) which has been amplified/colonized to increase the CFU concentration. The second barrel 312 of the dual-barrel syringe 300 is initially filled with a lysis buffer which is useful for breaking-down the assay sample. In the described embodiment, the second barrel 312 may contain approximately three hundred micro-liters (300 µl) of a lysis buffer.

The method for preparing the fluid sample for subsequent use in a portable assay sample system will be described in greater detail herein below. Suffice to say at this juncture that, of the various components provided as part of an aggregate kit, i.e., a kit for identifying a particular attribute of a fluid/food sample, a dual-barrel syringe 300 will be provided wherein: (i) the first barrel 308 is significantly larger in volume than the second barrel 312, (ii) the first barrel 308 is initially empty to allow it to be used for drawing and dispensing an assay sample through a lysis filter, and (iii) the second barrel 312 is completely filled with a lysis buffer and dispensed in stages to properly prepare the assay sample.

Returning to FIG. 16, a first step of the preparation method involves preparing the biological food sample 350 in a conventional manner such that the biological food sample 350 is amplified/colonized to increase its Colony Forming Unit (CFU) count or concentration. In a second step, the plunger 318 of the first barrel is depressed to its bottom position and the selection valve 304 is rotated to align the aperture 338 of the first barrel 308 with the nozzle passageway of the selector valve 304. The nozzle 330 of the selector value 304 is then placed in the prepared/pre-treated food sample 350, and the plunger 318 is raised to draw the fluid/food sample into the first barrel 308.

Figure 17:
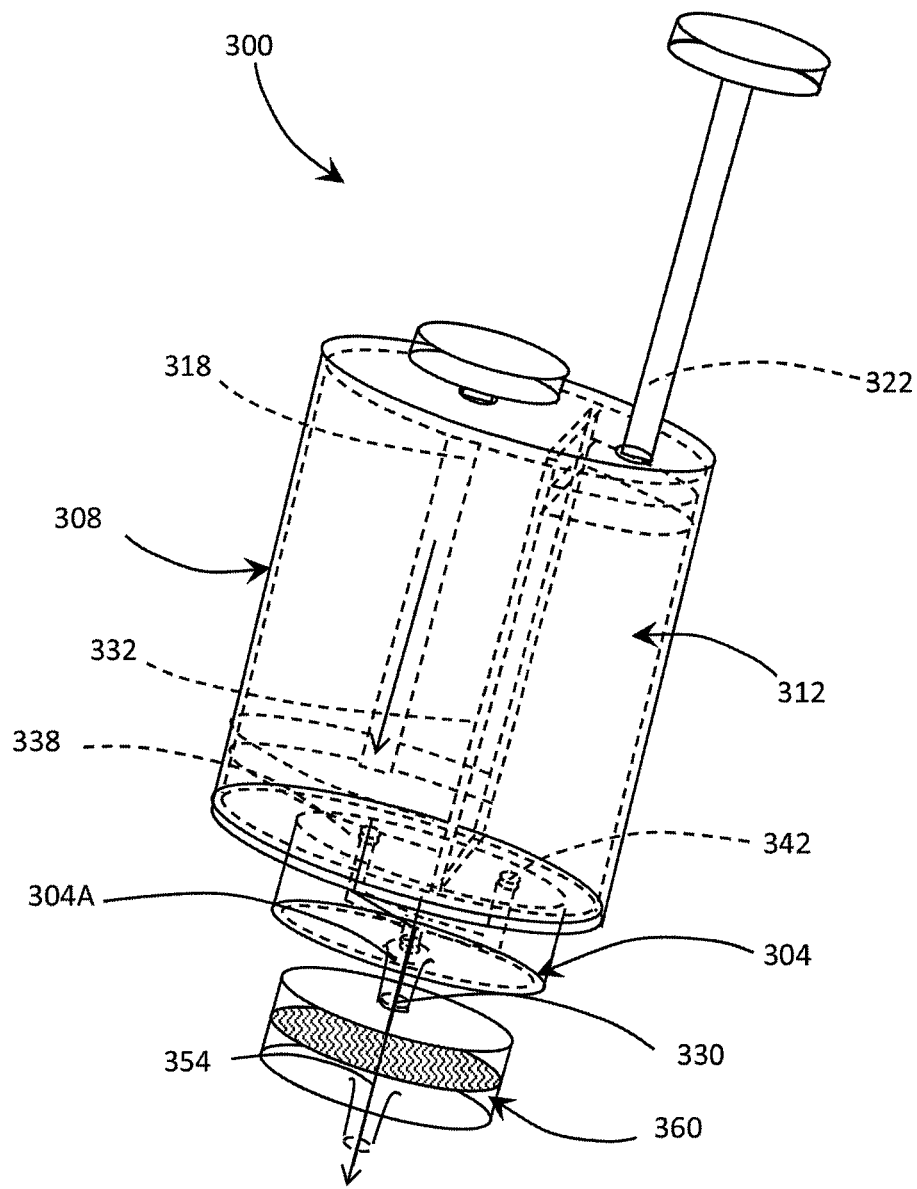

In FIG. 17, a third, or subsequent step, involves depressing the plunger 318 of the first barrel 308 to dispense the entire contents/volume of the first barrel 308 through a lysis filter 354 within a lysis module 360. The filter media 354 contains a filter material of appropriate porosity to extract the bacterial content of the fluid/food sample with high efficiency. Once all of the assay sample has been captured by the lysis filter 354, the selector valve 304 is rotated from the aperture 338 associated with the first barrel 308 to the aperture 342 associated with the second barrel 312.

Figure 18:
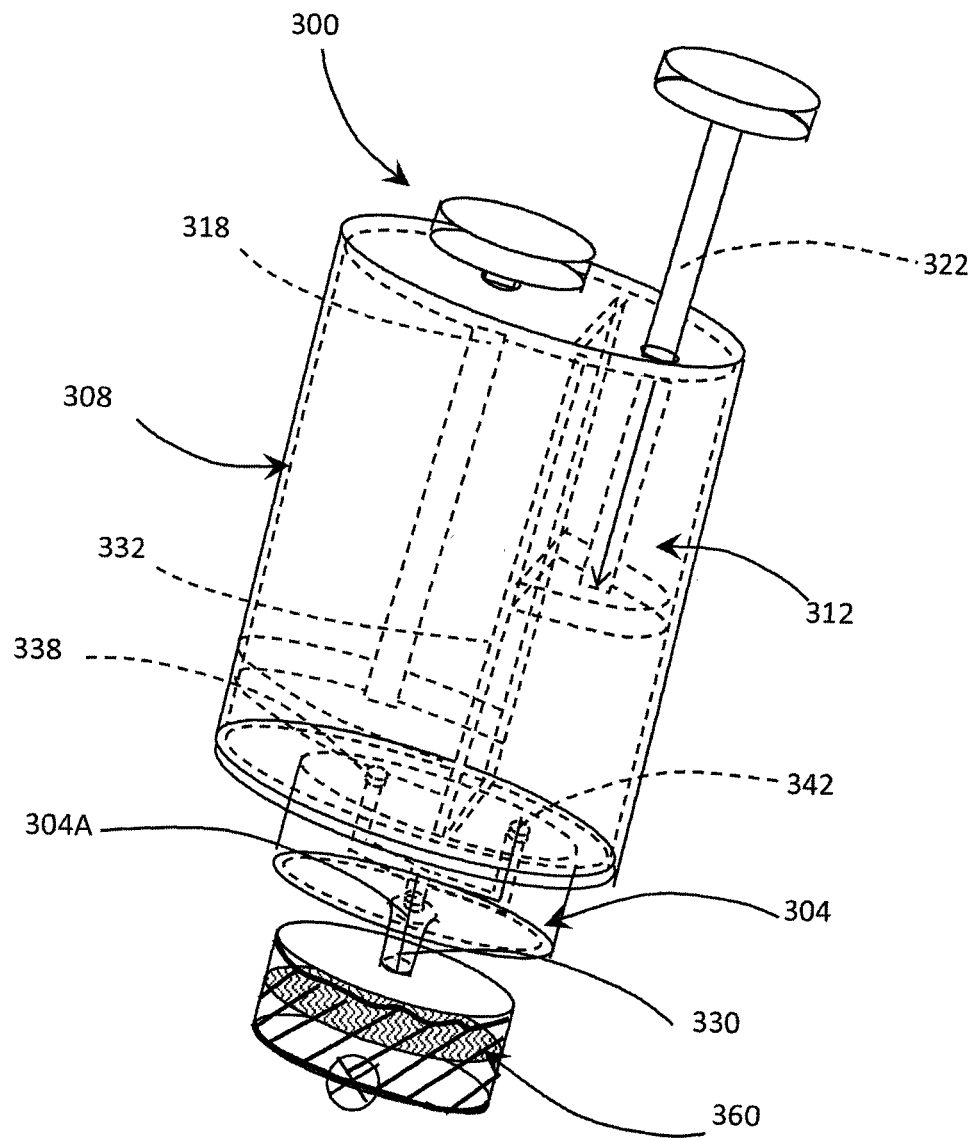

In FIG. 18, a fourth step involves dispensing a portion of the lysis buffer from second barrel 312 into the lysis module 360. In the described embodiment, about one-half of the lysis buffer is dispensed in the lysis module 360. Further, the lysis module 360 is closed in this step to allow the module 360 to hold the contents of the syringe 300, i.e., the lysis buffer, for a predetermined minimum period of time. In the described embodiment, the filtered contents of the lysis filter 354 are exposed into the lysis buffer for a period of at least five minutes (5 mins.), and preferably for as much as fifteen minutes (15 mins.) The lysis buffer breaks-down and liberates the nucleic acids within the lysed material for subsequent analysis. In certain embodiments, the time period of exposure may be automated such that the timing is controlled by computer software. In yet other embodiments, the lysis module 360 may be heated to facilitate and accelerate the lysis reactions.

Figure 19:
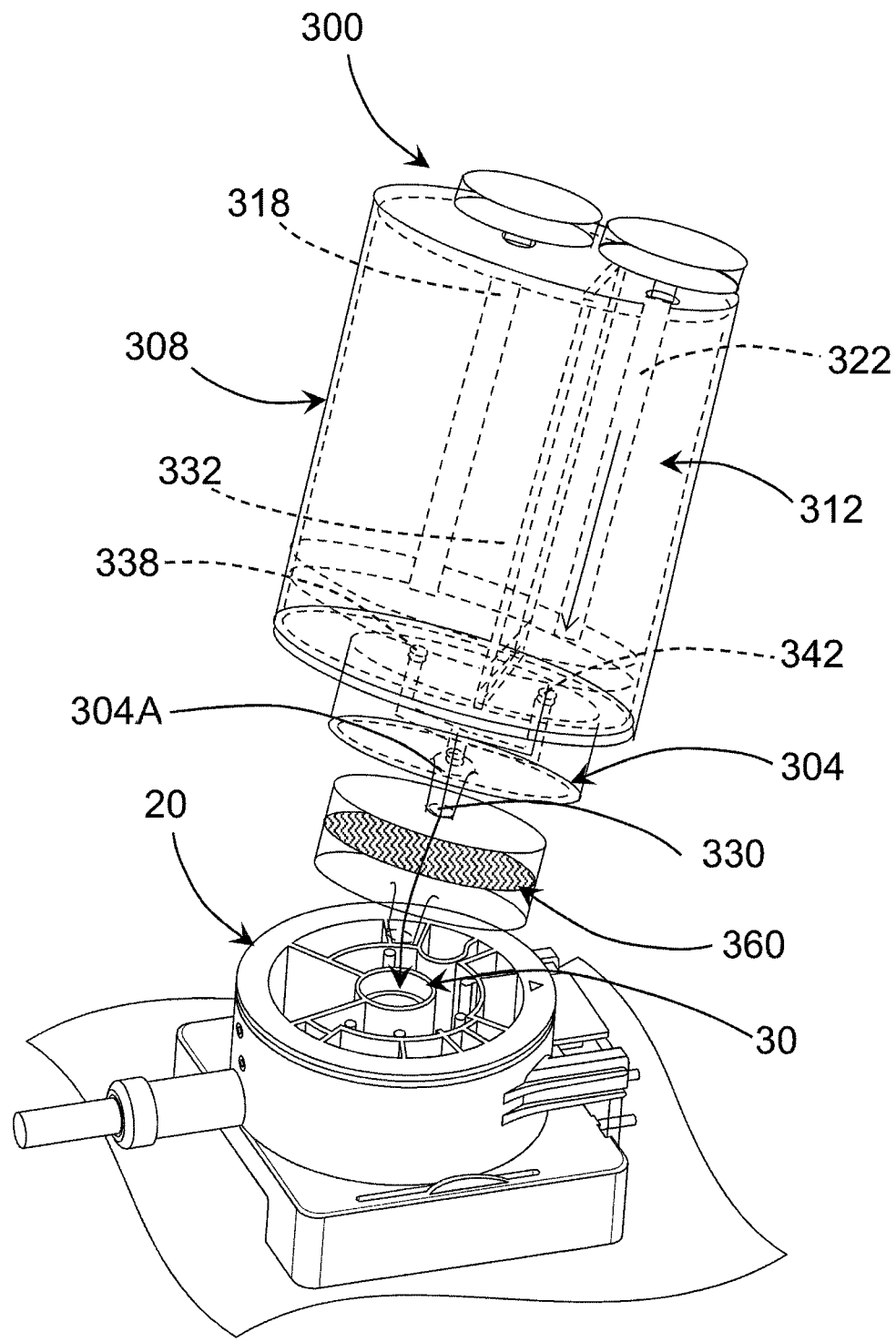

In FIG. 19, a fifth, and final, step involves flushing/rinsing the remaining portion of the lysis buffer, i.e., the remaining one-hundred and fifty micro-liters (150 µl,) through the lysis module 360 into the sample chamber 30 of the disposable cartridge 20. In other embodiments, the fluid/food sample could be purged into any suitable sample container based on the subsequent analysis to be provided/envisioned.

As mentioned above, this method allows for the detection of samples having a low CFU concentration in a sample by providing higher concentrations depending on the relative size of the syringe 300 and the lysis module 360. This method has the added benefit of extracting the relevant sample from the high salt broths often used in cultured food samples which have, in the past, been problematic for DNA purification and subsequent Polymerase Chain Reactions (PCRs.)

EXAMPLE

In one example, a particular attribute of a food/fluid sample was to be detected based on a desired Colony Forming Unit (CFU)/ml. A ten milliliter (10 ml) sample was extracted from a broth produced by growing bacteria from a twenty-five gram (25 g) sample of ground beef. The selector valve 304 is switched to flow the 10 ml sample through a one hundred and fifty micro-liter (150 µl) lysis module 360 containing a filter medium 354 to extract the bacterial content in the sample. After extraction, one hundred and fifty micro-liters (150 µl) of a lysis buffer was injected into the to the lysis module 360 and allowed to react for approximately 5 minutes. After the prescribed time period, another one hundred and fifty micro-liters (150 µl) of the lysis buffer is dispensed through the filter medium 354 to cause the entire 300 micro-liters (300 µl) to be flushed into the sample chamber 30 of the disposable cartridge 20. The lysed DNA material is then flushed through into an assay cartridge While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

What is claimed is:

1. A system for preparing a fluid sample for assay testing of a fluid attribute, comprising:
    a dual plunger syringe comprises first and second barrels sharing a common wall, and a rotating valve mechanism containing a nozzle in fluid communication with each of the barrels, the first barrel being empty and configured to receive a quantity of the sample fluid, the second barrel being filled with a lysis buffer;
    a filter configured to receive the sample fluid by rotating the valve mechanism to the first barrel and dispensing the sample fluid through the filter, the filter capturing the fluid attribute so as to produce a sample-containing filter,
    a lysis module defining a container for receiving the sample-containing filter, the container being filled with the lysis buffer from the second barrel by rotating the valve mechanism of the dual syringe plunger to receive a first portion of the lysis buffer through the nozzle of the valve mechanism, and,
    a disposable cartridge operative to receive the fluid sample to assay the fluid attribute, the fluid sample being received within an assay cavity upon opening the lysis module and dispensing a second portion of the lysis buffer from the second barrel through the nozzle of the valve mechanism to flush the sample-containing filter with the second portion of the lysis buffer as the fluid sample is received within the assay cavity.

2. The system of claim 1, wherein the first and second barrels define first and second volumes, respectively, the first volume being larger than the second volume.

3. The system of claim 1, wherein the first and second barrels define first and second volumes, respectively, the first volume being five to one-hundred times larger than the second volume.

4. The system of claim 1, wherein about one-half of the lysis buffer from the second barrel fills the lysis module and about one-half of the lysis buffer from the second barrel flushes the sample containing filter within the lysis module.

5. The system of claim 1, further comprising a heater operative to heat the lysis module while the lysis buffer breaks down the material of the fluid sample.

* * * * *